United States Patent [19]

Patton

[11] Patent Number: 5,157,169

[45] Date of Patent: Oct. 20, 1992

[54] PREPARATION OF 3-HALO-HALOBENZENES AND 1-HALO-3,5-DIHALOBENZENES

[75] Inventor: Jerry R. Patton, Ballwin, Mo.

[73] Assignee: Mallinckrodt Specialty Chemicals Company, St. Louis, Mo.

[21] Appl. No.: 857,821

[22] Filed: Mar. 26, 1992

[51] Int. Cl.$^5$ .................. C07C 25/13; C07C 17/10
[52] U.S. Cl. .................. 570/143; 570/147; 570/206
[58] Field of Search ............... 570/143, 147, 206, 207

[56] References Cited

U.S. PATENT DOCUMENTS 5,053,542 10/1991 Patton .................. 564/412

Primary Examiner—Howard T. Mars
Assistant Examiner—Kimberly J. Kestler
Attorney, Agent, or Firm—Rothwell, Figg, Ernst & Kurz

[57] ABSTRACT

In a process for producing a 3-halo-halobenzene or a 1-halo-3,5-dihalobenzene, a 2-halo-4-haloaniline or 2-halo-4,6-dihaloaniline is mixed with a deaminating agent. The 2-halo-4-haloaniline or 2-halo-4,6-dihaloaniline is deaminated so as to form a corresponding 3-halo-halobenzene or 1-halo-3,5-dihalobenzene.

11 Claims, No Drawings

PREPARATION OF 3-HALO-HALOBENZENES AND 1-HALO-3,5-DIHALOBENZENES

BACKGROUND OF THE INVENTION

1. Field of the Invention

The present invention relates to the field of haloaromatics.

2. Description of the Background Art

Haloaromatics, their production, and the reactions in which they are used, are of great interest in organic chemistry since haloaromatics are important in the production of industrial, pharmaceutical and agricultural chemicals.

While many methods for producing haloaromatics are known, because of their great commercial importance, there remains a need in the art for new and improved methods for producing haloaromatics which are more efficient and/or less expensive than prior art methods.

SUMMARY OF THE INVENTION

In accordance with the present invention, a process for producing a 3-halo-halobenzene or a 1-halo-3,5-dihalobenzene comprises forming a mixture of a deaminating agent and a first member selected from the group consisting of 2-halo-4-haloaniline and 2-halo-4,6-dihaloaniline, and deaminating said first member so as to form a corresponding second member selected from the group consisting of 3-halo-halobenzene and 1-halo-3,5-dihalobenzene.

DETAILED DESCRIPTION OF THE PREFERRED EMBODIMENTS

Starting materials for the process of the present invention can be selected from the group consisting of 2-haloanilines (such as 2-fluoroaniline), 4-haloanilines (such as 4-fluoroaniline), 2,4-dihaloanilines (such as 2,4-difluoroaniline) as well as mixtures thereof.

The starting material is mixed with a halogenating agent, which can be represented by the formula $X_2$, wherein X is a halogen such bromine, chlorine and the like. In preferred embodiments, X is bromine. Tetrabutylammonium trihalides (such as tetrabutylammonium tribromide) work well as halogenating agents.

The starting material is halogenated with the halogenating agent, under halogenating conditions, (e.g., at about 10°) in a suitable aprotic solvent (e.g., $CH_2Cl_2$, 1,2-dichloroethane, toluene, fluorobenzene, and the like) so as to form a corresponding 2-halo-4-haloaniline or 2-halo-4,6-dihaloaniline, which usually is isolated as the hydrohalide salt.

In accordance with the present invention, the 2-halo-4-haloaniline or 2-halo-4,6-dihaloaniline thus formed is mixed with a deaminating agent, such as $NaNO_2$ and $H_3PO_2$ (hypophosphorous acid). The 2-halo-4-haloaniline or 2-halo-4,6-dihaloaniline then is deaminated under deaminating conditions, so as to form a corresponding 3-halo-halobenzene or 1-halo-3,5-dihalo-halobenzene. The deamination is run in aqueous acid (e.g., HCl, HBr, $H_2SO_4$, or the like) by diazotizing the amine at about 0°–5° C. and then adding hypophosphorous acid before the decomposition.

In the above-described process wherein the 3-halo-halobenzene is formed, the 2-halo-4-haloaniline is provided as 2-halo-4-haloaniline.HX if the halogenating agent utilized is $X_2$.

When the original starting material is selected from the group consisting of 2-fluoroaniline, 4-fluoroaniline, 2,4-difluoroaniline and mixtures thereof, and the halogenating agent is $Br_2$, the corresponding 2-halo-4-aniline formed is selected from the group consisting of 2-bromo-4-fluoroaniline, 4-bromo-2-fluoroaniline, 2-bromo-4,6-difluoroaniline and mixtures thereof. Deamination of this product in accordance with the present invention, as described above, provides a desired end product, 3-bromofluorobenzene, and 1-bromo-3,5-difluorobenzene.

In a particularly preferred embodiment of the present invention, $Br_2$ is mixed with a starting material selected from the group consisting of 2-fluoroaniline, 4-fluoroaniline, 2,4-difluoroaniline or a mixture thereof. The $Br_2$ is reacted with the selected starting material to form a corresponding intermediate material selected from the group consisting of 2-bromo-4-fluoroaniline.HBr, 4-bromo-2-fluoroaniline.HBr, 2-bromo-4,6-difluoroaniline.HBr and mixtures thereof. The resulting intermediate material then is mixed with a deaminating agent comprising $NaNO_2$ and $H_3PO_2$. The intermediate material then is deaminated, under deaminating conditions, so as to form the desired end product, 3-bromofluorobenzene or 1-bromo-3,5-difluorobenzene.

The invention is further illustrated by the following examples, which are not intended to be limiting.

Since many modifications, variations and changes in detail may be made to the described embodiments, it is intended that all matter in the foregoing description be interpreted as illustrative and not in a limiting sense.

EXAMPLE I

Preparation of 3-Halo-Halobenzenes

In a suitable aprotic solvent (e.g., $CH_2Cl_2$, toluene, fluorobenzene, or the like) 1 mole of tetrabutylammonium bromide is dissolved and stirred as 1 mole of $Br_2$ (bromine) is added. This mixture of tetrabutylammonium trihalide and solvent is cooled to 10° before 1 mole of 2-fluoroaniline or 4-fluoroanilin, or a mixture of both, is added. The reaction takes place immediately to produce 4-bromo-2-fluoroaniline.HBr, or 2-bromo-4-fluoroaniline.HBr, or a mixture of the two. The salt is then collected and dried before carrying it up to the next step. Catalyst and solvent are recovered for recycle.

The deamination is run in aqueous acid (e.g., HCl, HBr, $H_2SO_4$, or the like) by diazotizing the amine at about 0°–5° C. and then adding hypophosphorous acid before the decomposition. One mole of the aniline salt is slurried in aqueous HCl as one mole of $NaNO_2$ dissolved in water is added at 0° to 5° C. The mixture goes into solution and 1.1 to 1.5 moles of 30 to 50% aqueous hypophosphorous acid then is added at 0° to 5° C. The reaction then is controlled to <30° C. by cooling as nitrogen gas is evolved to give the desired 3-bromofluorobenzene in 80–85% yield.

Either bromine or chlorine can be used for the halogen source and any 2 or 4 substituted aniline will give the corresponding 3-halo-substituted halobenzene. Halogenation of aromatic amine compounds is described in commonly owned U.S. Pat. No. 5,053,542 and U.S. Ser. No. 07/641,396, filed Jan. 15, 1991.

EXAMPLE 11

Preparation of 1-Halo-3,5-Dihalobenzenes

In a suitable aprotic solvent (e.g., $CH_2Cl_2$, 1,2-dichloroethane, toluene, fluorobenzene, or the like), 1 mole of 2,4-dihaloaniline, such as 2,4-difluoroaniline is dissolved. The reaction mixture is cooled to about 10° C. and one mole of Bromine is added. There will be an immediate reaction with an exotherm, which can be held to 30° C. The slurry of 2-bromo-4,6-difluoroaniline hydrobromide then is filtered and the solvent recycled for the next run. The solid then is dried.

In accordance with the above process, I have achieved a yield of 2-bromo-4,6-difluoroaniline.HBr (95%) of 98%. Aqueous diazotization of 1 mole of 2-bromo-4,6-difluoroaniline hydrobromide in aqueous HCl using 1.1–1.10 moles of $NaNO_2$ at 0°–5° afforded a solution of diazonium salt. Hypophosphorous acid (1.5 moles) was added at less than 5° C. and the solution was allowed to warm to 15° C. with nitrogen evolution. After stirring for one hour, the mixture was decanted and extracted with an appropriate organic solvent to yield 75% (mole basis) of the desired 1-bromo-3,5-difluorobenzene, distilled yield of 99+% pure material. Other 1-bromo-3,5-dihalobenzenes were similarly prepared.

I claim:

1. A process for producing a 3-halo-halobenzene or a 1-halo-3,5-dihalobenzene, comprising forming a mixture of a deaminating agent and a first member selected from the group consisting of 2-halo-4-haloaniline and 2-halo-4,6-dihaloaniline, and deaminating said first member, so as to form a corresponding second member selected from the group consisting of 3-halo-halobenzene and 1-halo-3,5-dihalobenzene.

2. The process of claim 1 further including the step of providing said first member by forming a mixture of a halogenating agent and a starting material selected from the group consisting of 2-haloanilines, 4-haloanilines, 2,4-dihaloanilines, and mixtures thereof, and halogenating said starting material with said halogenating agent so as to form said first member.

3. The process of claim 2 wherein said halogenating agent is a tetrabutylammonium trihalide.

4. The process of claim 2 wherein said halogenating agent is represented by the formula $X_2$, wherein X is halogen.

5. The process of claim 4 wherein said 2-halo-4-haloaniline is provided as 2-halo-4-haloaniline.HX.

6. The process of claim 5 wherein said starting material is selected from the group consisting of 2-fluoroaniline, 4-fluoroaniline, 2,4-difluoroaniline and mixtures thereof.

7. The process of claim 6 wherein X is bromine.

8. The process of claim 7 wherein said first member is selected from the group consisting of 2-bromo-fluoroaniline, 4-bromo-2-fluoroaniline, 2-bromo-4,6-difluoroaniline, mixtures thereof, and their HBr salts.

9. The process of claim 8 wherein said deaminating agent includes $NaNO_2$ and $H_3PO_2$.

10. A process for producing 3-bromo-fluorobenzene, comprising:
   a) forming a mixture of tetrabutylammonium tribromide and a starting material selected from the group consisting of 2-fluoroaniline, 4-fluoroaniline and a mixture thereof;
   b) reacting said tetrabutylammonium tribromide and said starting material to form an intermediate material selected from the group consisting of 2-bromo-4-fluoroaniline.HBr, 4-bromo-2-fluoroaniline.HBr and a mixture thereof;
   c) forming a mixture of said intermediate material and a deaminating agent comprising $NaNO_2$ and $H_3PO_2$; and
   d) deaminating said intermediate material so as to form 3-bromo-fluorobenzene.

11. A process for producing 1-bromo-3,5-difluorobenzene comprising:
   a) reacting 2,4-difluoroaniline with $Br_2$ so as to form 2-bromo-4,6-difluoroaniline.HBr;
   b) forming a mixture of said 2-bromo-4,6-difluoroaniline.HBr and a deaminating agent comprising $NaNO_2$ and $H_3PO_2$; and
   c) deaminating said 2-bromo-4,6-difluoroaniline.HBr so as to form 1-bromo-3,5-difluorobenzene.

* * * * *